United States Patent [19]

Arnould et al.

[11] Patent Number: 5,013,731

[45] Date of Patent: May 7, 1991

[54] CEPHALOSPORIN COMPOUNDS

[75] Inventors: Jean C. Arnould, Cormontreuil; Jean J. Lohmann, Hermonville; Georges Pasquet, Bazancourt, all of France

[73] Assignee: ICI Pharma, Cergy Cedex, France

[21] Appl. No.: 512,069

[22] Filed: Apr. 19, 1990

Related U.S. Application Data

[63] Continuation of Ser. No. 936,721, Nov. 25, 1986, abandoned.

[30] Foreign Application Priority Data

Nov. 27, 1985 [EP] European Pat. Off. ........ 85402331.4

[51] Int. Cl.$^5$ ................ C07D 501/18; A61K 31/545
[52] U.S. Cl. .................... 514/202; 514/201; 540/222; 540/226; 540/227; 540/230
[58] Field of Search ............... 540/221, 222; 514/202, 514/201

[56] References Cited

U.S. PATENT DOCUMENTS

| | | | |
|---|---|---|---|
| 4,024,133 | 5/1977 | Cook | 260/243 C |
| 4,033,950 | 7/1977 | Cook | 260/243 C |
| 4,138,555 | 2/1979 | Cook | 544/22 |
| 4,252,802 | 2/1981 | Denzel | 424/246 |
| 4,278,793 | 7/1981 | Dürckheimer | 544/21 |
| 4,439,433 | 3/1984 | Heymes | 424/246 |
| 4,474,779 | 10/1984 | Nagano | 424/246 |
| 4,647,556 | 3/1987 | Lattrell | 514/206 |
| 4,678,781 | 7/1987 | Jung | 540/225 |

FOREIGN PATENT DOCUMENTS

| | | |
|---|---|---|
| 197409 | 10/1956 | European Pat. Off. . |
| 0018155 | 10/1980 | European Pat. Off. . |
| 2068958 | 8/1981 | United Kingdom . |
| 2071664 | 9/1981 | United Kingdom . |
| 2105719 | 3/1983 | United Kingdom . |

Primary Examiner—Nicholas S. Rizzo
Attorney, Agent, or Firm—Cushman, Darby & Cushman

[57] ABSTRACT

A cephalosporin derivative of the formula I:

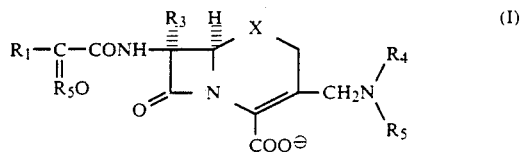

in which X is S, O, $CH_2$ or SO,

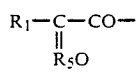

represents one of the C-7 acyl groups known in the cephalosporin art, R3 is hydrogen or methoxy, R4 is hydrogen, optionally substituted alkyl, allyl, furfuryl or benzyl, and R5 is an aromatic heterocyclic ring system which is linked via carbon, and which contains a quaternized nitrogen atom.

20 Claims, No Drawings

CEPHALOSPORIN COMPOUNDS

This is a continuation of application No. 06/936,721, filed on Nov. 25, 1986, which was abandoned upon the filing hereof.

This invention relates to cephalosporin derivatives which have antibacterial activity.

According to the invention there is provided a cephalosporin derivative of the formula I (formulae given hereinafter) in which X is sulphur, oxygen, methylene or sulphinyl (R or S configuration):

R1 is 2-aminothiazol-4-yl or 2-aminooxazol-4-yl each optionally substituted in the 5–-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R50 is chloromethylene or a radical of the formula $=N.O.R2$, wherein R2 is hydrogen, (1–6C)alkyl, (3–8C)cycloalkyl, (1–3C)alkyl(3–6C)cycloalkyl, (3–6C)cycloalkyl(1 3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkylcarbamoyl(1–4C)alkyl, (1–4C)haloalkylcarbomoyl(1–4C)alkyl, triphenylmethyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2 oxopyrrolidinyl, or 2 oxotetrahydro furan 3-yl, or —R2 is of the formula —$(CH_2)_n$—R6 in which n is 1 to 4 and R6 is piperidino, pyrrolidino, morpholino, piperazino or N-methylpiperazino, each value of R6 being optionally substituted by (1–4C)alkyl, phenyl or benzyl, or —R2 is of the formula —$(CH_2)_m$—W—R7 in which m is 0 to 3, W is sulphur or a direct bond, and R7 is phenyl or pyridinio(1–4C)alkylene or R7 is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of R7 being optionally substituted, where possible, by one or two groups selected from (1–4C)alkyl, amino, hydroxy, carboxy, carbamoyl, nitro, (2–5C)alkoxycarbonyl, cyano or sulpho, or R2 is of the formula —$(CH_2)_n$—CO—R8 in which n is 1 to 4 and R8 is (1–4C)alkyl, phenyl or benzyl, or —R2 is of the formula —COR9 or —$(CH_2)_n$—OCO—R9 in which n is 1-4 and R9 is hydrogen, (1–4C)alkyl, (1–4C)haloalkyl, phenyl or benzyl, such a phenyl or benzyl group being optionally substituted by 1, 2 or 3 substituents selected from (1–6C)alkyl, (2–6C)alkanoyloxy and hydroxy groups, or —R2 is of the formula —G—$CH_2$—R10 in which G is carbonyl or a direct bond and R10 is phthalimido, or —R2 is of the formula — NR11R12R13 in which R11, R12 and R13 are (1–4C)alkyl, or R11 is (1–4C)alkyl and R12 and R13 are joined to form a (3–6C)carbocyclic ring, or R11, R12 and R13 are joined to form a 1-azonia-4-azabicyclo[2,2,2]octane or 1-azonia-3,5,7 triazatricyclo[3,3,1,1$^{3,7}$]decane, or —R2 is of the formula II in which p is 1 or 2 and R14 and R15 are hydrogen or (1–4C)alkyl, or —R2 is of the formula —P(O)R16R17 in which R16 is hydroxy, (1–4C)alkoxy, (2–8C)dialkylamino, phenoxy, phenylamino or one of the values given above for R6, and R17 is (1–4C)alkyl, (1–4C)alkoxy (2–8C)dialkylamino, phenoxy, phenylamino, piperidino, pyrrolidino, morpholino, piperazino or N-methylpiperazino, or —R2 is of the formula —$CH_2P(O)R18R19$ in which R18 and R19 are hydroxy or (1–4C)alkoxy, or —R2 is of the formula —CH(SR20)COOR21 in which R20 is (1–4C)alkyl and R21 is hydrogen or (1–6C)alkyl, or —R2 is of the formula III in which m is O–3, R22 is hydrogen, (1–3C)alkyl or methylthio, R23 is hydrogen, (1–3C)alkyl, ($C_3$-$C_7$) cycloalkyl, cyano, carboxy, (2–5C)carboxyalkyl or methanesulphonylamino, or phenyl optionally substituted by amino or hydroxy, or R22 and R23 are joined to form, together with the carbon to which they are attached, a (3–7C) carbocyclic ring, and R24 is hydroxy, amino, (1–4C)alkoxy, (1–4C)alkylamino, phenylamino or of the formula R6 given above or of the formula NHOR25 in which R25 is hydrogen, (1–4C)alkyl, phenyl or benzyl, or R2 is of the formula — ✕CH(COOH)Ph wherein Ph represents a benzene ring optionally substituted by 1, 2 or 3 substituents selected from (1–6C)alkyl, (2–6C)alkanoyloxy and hydroxy groups and wherein the chiral centre denoted by ✕ may have either the R or S absolute configuration or be a racemate thereof: provided that when R2 contains phenyl, and unless otherwise stated, the phenyl is optionally substituted by 1 or 2 groups selected from halogen, hydroxy, amino, carboxy, nitro, carbamoyl, cyano and aminomethyl, R3 is hydrogen or methoxy;

R4 is hydrogen, (1–4C)alkyl, halo(1–4C)alkyl, hydroxy(1–4C)alkyl, (1–4C)alkoxy(1–4C)alkyl, carboxy (1-4)alkyl, amino (1–4C)alkyl, cyano(1–4C)alkyl, (1–4C)alkanoylamino(1–4C)alkyl, allyl, furfuryl, benzyl or pyridyl(1–4C)alkyl R5 is an aromatic heterocyclic fused ring system which is linked via carbon and is one of the formula IV to X inclusive in which W, Y and Z are selected from O, S, N, $CR^{26}$ (in which $R^{26}$ is selected from hydrogen, halogen, (1–6C)alkyl, carboxy, (2–6C)alkoxy carbonyl, (2–6C) alkoxycarbonyl(1–4C)alkyl, (1–6C)-alkoxy, (1–6C)alkylthio, cyano, (2–4C)cyanoalkyl, amino, (1–6C)alkylamino, (2–8C)dialkylamino, benzylamino (optionally substituted in the benzene ring thereof by nitro), thenylamino, allylamino, (1–6C)aminoalkylamino, (1–6C)alkoxy(1–6C)alkylamino, (1–6C)hydroxyalkylamino, hydroxy, mercapto, carbamoyl, (2–6C)alkylcarbamoyl, (3–10C)dialkylcarbamoyl, phenylthio and heteroarylthio wherein heteroaryl is a 5- or 6-membered ring containing 1, 2 or 3 hetero atoms selected from oxygen, nitrogen and sulphur) and $NR^{27}$ (in which $R^{27}$ is selected from hydrogen, (1–6C)alkyl, phenyl or benzyl, which alkyl, phenyl or benzyl groups may be substituted when and where possible by one or two groups selected from halogen, nitro, (1–6C)alkyl, hydroxy, (1–4C)alkoxy, carboxy, cyano, (2–6C)alkoxycarbonyl, carbamoyl, sulphamoyl, sulpho, mono or di(1–4C)alkylcarbamoyl, or mono or di (1–4C)alkylsulphamoyl) provided that (i) only one of W, Y and Z can represent S or O;

(ii) in formulae IV and V, Y must be other than $CR^{26}$;

(iii) in formula V one of W and Z must be other than CR$^{26}$ and (iv) in formula IX neither W nor Z can be S and W cannot be O;

R$^{28}$ is attached to carbon and is selected from the atoms and groups listed above in respect of R$^{26}$; and R$^{29}$ is selected from hydrogen, (1-6C)alkyl, (1-6C)alkyl(2-6C)alkenyl, (1-6C)alkoxy, (2-6C)alkoxyalkyl, carboxy(1-6C)alkyl, [(1-6C)alkoxy]carbonyl(1-6C)alkyl, carbamoyl(1-6C)alkyl, mono or di(1-4C)alkylamino(1-6C)alkyl, carboxyaminocarbonyl(1-6C)alkyl, [(1-6C)alkoxy]carbonylaminocarbonyl(1-6C)alkyl, (2-8C)alkanoyl]methyl, benzoylmethyl(1-6C)hydroxyalkyl, amino, (1-6C)alkylamino, (1-6C)aminoalkyl, phenyl(1-6C)alkyl, phenyl(1-6C)alkoxy, (3-6C)cycloalkyl, (3-6C)cycloalkenyl, cyano(3-6C)cycloalkenyl, mono or di(1-4)alkylcarbamoyl(1-6C)alkyl or (1-4C)alkoxy(2-4C)alkoxy(1-4C)alkyl or phenyl optionally substituted by 1 or 2 groups selected from halogen, (1-6C)alkyl, (1-6C)alkoxy, hydroxy, amino, carboxy, nitro, carbamoyl, cyano, trifluoromethyl, aminomethyl, (1-4C)alkanoyl, (1-6C)alkanoylamino, halo(1-4C)alkyl, (2-6C)alkoxycarbonyl, mono- or di(1-4C)alkylcarbamoyl, mesyl, vinyl, sulpho, sulphamoyl, or mono- or di(1-4C)alkylsulphamoyl; or (2-6C)alkenyl optionally substituted by halogen, cyano, carbamoyl, mono- or di-(1-4C)alkylcarbamoyl, piperidinocarbonyl, morpholinocarbonyl, 2-ureidoethyl, 2-thioureidoethyl, 2-(thioacetylamino)ethyl, sulphamoyl, 2-amino-2-carboxyethyl, acetylaminomethyl, phthalimidomethyl, 4-5-dihydroimidazol-2-ylmethyl, 3,4,5,6 tetrahydropyrimidin-2-ylmethyl, 2-(1,2,3,6-tetrahydro-2,6-dioxopurin-7-yl)ethyl, 2hydroxyiminopropyl (syn or anti) or 2[(1-C)alkoxyimino]propyl (syn or anti) or cyano(1-4C)alkyl:

or R$^{29}$ is of the formula —(CH$_2$)$_2$—NR30R31R32 in which R30, R31 and R32 are (1-4C)alkyl, or R$^{29}$ is of the formula —(CH$_2$)$_q$—R33 in which q is 0—2 and —R33 is pyridine, pyridazine, pyrimidine, pyrazine, 1,2,5,6-dihydro-5,6-dioxo-1,2,4-triazine, 2-[(1-4C)alkyl]-1,2,5,6-dihydro-5,6-dioxo-1,2,4-triazine, 1-[(1-4C)alkyl]tetrazole, furan, thiophene, pyrrole, 1-[(1-4C)alkyl]pyrrole, oxazole, thiazole, imidazole, 1-[1-4C)alkyl]imidazole, isoxazole, isothiazole, pyrazole, 1,2,3 thiadiazole, 1-[(1-4C)alkyl]pyrazole, benzfuran, benzthiophene, indole, oxindole, 1 [(1-4C)alkyl]indole, benzoxazole, benzthiazole, benzimidazole, 1 [(1-4C)alkyl]benzimidazole, 3,4-dihydro-4-oxo-2-H-benzo[e]oxazine each of these ring systems being linked to (CH$_2$)$_q$ through carbon and each ring system being optionally substituted by halogen, amino, (1-6C)alkyl, (1-4C)haloalkyl, (3-6C)cycloalkyl, (2-6C)alkenyl, carboxy, (2-6C)alkoxycarbonyl, (1-6C)alkoxy, cyano, (2-6C)cyanoalkenyl, carbamoyl, mono or di(1-4C)alkylcarbamoyl, (1-4C)alkanoylamino, guanidino, hydroxy, nitro or amino:

or R29 is 2-guanidino-thiazol-4-ylmethyl, hydroxybenzoyl-methyl, 2-thenyl, 2-imidazolylmethyl or cinnamyl, optionally substituted by halogen, (1-6C)alkyl, hydroxy, (1-4C)alkoxy, carboxy, (2-6C)alkoxycarbonyl, nitro or carbamoyl;

or R29 is —(CH$_2$)$_t$NHCOR34 or —(CH$_2$)$_t$S(O)$_s$—R34 in which t is 1-6, s is 0, 1 or 2, and R34 is (1-6C)alkyl or (1-6C)alkoxy, or R29 is of the formula (CH$_2$)$_2$N=CR36NR37R38 or —(CH$_2$)$_n$C(NR36)NR37R38 or a tautomer thereof in which n is 1-6 and R36, R37, R38 are hydrogen or (1-4C)alkyl and the N oxides thereof where chemically possible:

and the salts formed with acids and bases which afford pharmaceutically acceptable anions and cations respectively.

It is to be understood that in the above formula I and throughout this specification, the illustrated stereochemistry of the ceph 3 em nucleus, and its optional modifications at the 1 position, is the absolute configuration. It is also to be understood that, since R5 contains a quaternary nitrogen, the compounds of the formula I will normally exist in zwitterionic form, involving the quaternary nitrogen and the carboxy group. When the compound of the formula I contains further acidic or basic substituents, it is to be understood that the possibility of a double zwitterionic form of the compound will arise. Alternatively, exogenous anions or cations may be included, to form pharmaceutically-acceptable base addition or acid addition salts, as defined above.

A particular value for R2 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloroethyl, 2-fluoroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N aminoamidino)ethyl, tetrahydropyran-2-yl, thietan-3-yl or 2-oxo tetrahydrofuran-3-yl, or, when R2 is of the formula —(CH$_2$)$_n$-R6 in which n is 1 to 4 and R6 is piperidino, pyrrolidino, morpholino, piperazino or N-methylpiperazino, a particular value of R2 is when each value of R6 is optionally substituted by methyl, phenyl or benzyl, or, when R2 is of the formula —(CH$_2$)$_m$—W—R7 in which m is 0 to 3, W is sulphur or a direct bond, particular values for R2 are when R7 is phenyl, pyridiniomethylene, 2-pyridinioethylene or R7 is pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R7 being optionally substituted, where possible, by one or two groups selected from methyl, amino, hydroxy, carboxy, carbamoyl, nitro, methoxycarbonyl, ethoxycarbonyl, cyano or sulpho, or, when R2 is of the formula —(CH$_2$)$_n$—CO—R8 in which n is 1 to 4, a particular value for R2 is when R8 is methyl, ethyl, phenyl or benzyl, or, when R2 is of the formula —COR9 or —(CH$_2$)$_n$—OCO—R9 in which n is 1-4, a particular value for R2 is when R9 is hydrogen, methyl, chloromethyl, bromomethyl, 2-chloroethyl, 2-bromoethyl, phenyl or benzyl, and a particular value for the optional substituent(s) on such a phenyl or benzyl group is methyl, acetyl or hydroxy, or, when R2 is of the formula —G—CH$_2$—R10, a particular value for R2 is when G is carbonyl or a direct bond and R10 is phthalimido, or, when R2 is of the formula — NR11R12R13, a particular value for R2 is when R11, R12 and R13 are methyl or ethyl, or R11 is methyl or ethyl and R12 and R13 are joined to form a cyclopropyl, cyclobutyl, cyclopentyl or cyclohexyl ring, or R11, R12 and R13 are joined to form a 1-azonia-4-azabicyclo[2,2,2]octane or 1-azonia-3,5,7-triazatricyclo[3,3,1,1^{3,7}]decane, or, when R2 is of the formula II in which p is 1 or 2, a particular value for R2 is when R14 and R15 are hydrogen or methyl, or when R2 is of the formula —P(O)R16R17, a particular value for R2 is when R16 is hydroxy, methoxy, ethoxy, dimethylamino, diethylamino, phenoxy, phenylamino, or one of the particular values given above for R6, and R17 is methyl, ethyl, methoxy, ethoxy, dimethylamino, diethylamino, phenoxy, phenylamino, piperidino, pyrrolidino, morpholino, piperazino or N-methylpiperazino, or, when R2 is of the formula —CH2P(O)R18R19, a particular value for R2 is when R18 and R19 are hydroxy, methoxy or ethoxy, or, when R2 is of the formula —CH(SR20)COOR21, a particular value for R2 is when R20 is methyl or ethyl and R21 is hydrogen, methyl, ethyl or isopropyl, or, when R2 is of the formula III in which m is 0-3, a particular value for R2, when m=0, is when R22 is hydrogen, methyl or methylthio, R23 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R23 and R24 are joined to form, together with the carbon to which they are attached, a cyclopropane, cyclobutane, cyclopentane, cyclohexane or cycloheptane ring and R25 is hydroxy, amino, methoxy, ethoxy, methylamino, ethylamino, phenylamino or one of the particular values for R6 given above or of the formula NHOR25 in which R25 is hydrogen, methyl, ethyl, phenyl or benzyl, or, when R2 is of the formula —$\overset{*}{X}$H(COOH)Ph, a particular value for the optional substituent(s) on the benzene ring is methyl, acetyl or hydroxy, provided that when R2 contains phenyl, and unless otherwise stated above, the phenyl is optionally substituted by 1 or 2 groups selected from fluorine, chlorine, bromine, hydroxy, amino, carboxy, nitro, carbamoyl, cyano and aminomethyl.

A particular value for R3 is hydrogen or methoxy.

A particular value for R4 is hydrogen, methyl, ethyl, n-propyl, isopropyl, 2-fluoroethyl, 2-chloroethyl, 2-hydroxymethyl, 2-methoxyethyl, carboxymethyl, (R) and (S)- 1-carboxyethyl, 2-aminoethyl, 2-cyanoethyl, 2-formamidoethyl, allyl, furfuryl, benzyl or 4-pyridylmethyl.

Particular values for the groups R26 and R28 (same or different) are hydrogen, fluorine, chlorine, bromine, methyl, ethyl, n-propyl, isopropyl, carboxy, methoxycarbonyl, ethoxycarbonyl, methoxycarbonylmethyl, ethoxycarbonylmethyl, methoxy, ethoxy, methylthio, ethylthio, cyano, cyanomethyl, 2-cyanoethyl, amino, methylamino, ethylamino, isopropylamino, dimethylamino, benzylamino, (optionally substituted in the benzene ring by nitro), allylamino, 2-aminoethyl-amino, 2-methoxyethylamino, 2-hydroxyethylamino, hydroxy mercapto, carbamoyl, methylcarbamoyl, ethylcarbamoyl, dimethylcarbamoyl, phenylthio and heteroarylthio in which the heteroaryl ring is a furan, thiophene, imidazole, thiazole, pyrazole, thiadiazole, pyridine, pyrimidine, pyrazine or pyridazine.

Particular values for the group R27 are hydrogen, methyl, ethyl, n-propyl, isopropyl, phenyl or benzyl, each optionally substituted by one or two groups selected from fluorine, chlorine, bromine, methyl, ethyl, n-propyl, isopropyl, hydroxy, carboxy and cyano.

Particular values for the group R29 are hydrogen, methyl, ethyl, n-propyl, isopropyl, t-butyl, methoxymethyl, 2-methoxyethyl, carboxymethyl, 2-carboxyethyl, methoxycarbonylmethyl, 2-methoxycarbonylethyl, carbamoylmethyl, 2-carbamoylethyl, carboxyaminocarbonylmethyl, 2-(carboxyaminocarbonyl)ethyl, methoxycarbonylaminocarbonylmethyl, 2-(methoxycarbonylaminocarbonyl)ethyl, acetylmethyl, propionylmethyl, benzoylmethyl, hydroxymethyl, 2-hydroxyethyl, methylamino, ethylamino, benzyl, 2-phenethyl, amino, cyclopropyl, cyclobutyl, methoxyethoxy, 2-methoxyethoxymethyl, mono- and dimethylcarbamoylmethyl, aminomethyl, 2-aminoethyl, 2-methylaminoethyl, 2-dimethylaminoethyl, 3-cyanocyclopent 2-enyl, 2-(3,4-dihydro 4-oxo H benzo[e]oxazin 2-yl)ethyl, benzyloxy or 2-phenylethoxy or of the formula (CH2)2—N=CR36NR37R38 or (CH2)2C(NR36)NR37R38 in which R36, R37 and R38 are hydrogen or methyl, —(—CH2)$_t$—NH—CO—R34 or —(CH2)$_t$—S(O)$_s$—R34 in which t is 1-6, s is 0, 1 or 2 and R34 is methyl, ethyl, methoxy or ethoxy, or phenyl optionally substituted by 1 or 2 groups selected from fluorine, chlorine, bromine, hydroxy, amino, carboxy, nitro, carbamoyl, cyano, trifluoromethyl, aminomethyl, methyl, ethyl, methoxy, ethoxy, acetyl, acetamido, methoxycarbonyl, ethoxycarbonyl, methylcarbamoyl, dimethylcarbamoyl, diethylcarbamoyl, mesyl and sulpho, or vinyl, allyl, 2,4-pentadienyl, 3-chloroallyl (cis and trans), 3-cyanoallyl, cyanomethyl, 3-cyanopropyl, 2-ureidoethyl, 2-thioureidethyl, 2-(thioacetylamino)ethyl, sulphamoyl, 2-amino-2-carboxyethyl, acetylaminomethyl, phthalimidomethyl, 4,5-dihydroimidazol-2-ylmethyl, 3,4,5,6-tetrahydropyrimidin-2-ylmethyl, 2-(1,2,3,6-tetrahydro 2,6-dioxopurin 7-yl)ethyl, 2-hydroxyiminopropyl (syn or anti), 2-(methoxyimino)propyl (syn or anti) or 2-(ethoxyimino)propyl (syn or anti), or of the formula —(CH2)2—NR30R31R32 in which R30, R31 and R32 are methyl or ethyl, or of the formula —(CH2)$_q$—R33 in which q is 0-2 and R33 is pyridine, pyridazine, pyrimidine, pyrazine, 1,2,5,6-dihydro-5,6-dioxo-1,2,4-triazine, 2-(methyl or ethyl) 1,2,5,6-dihydro-5,6-dioxo-1,2,4-triazine, 1-(methyl or ethyl)tetrazole, furan, thiophene, pyrrole, 1-(methyl or ethyl)pyrrole, oxazole, thiazole, imidazole, 1-(methyl or ethyl)imidazole, isoxazole, isothiazole, pyrazole, 1-(methyl or ethyl) pyrazole, 1,2,3-thiadiazole, benzfuran, benzthiophene, indole, 1-(methyl or ethyl)indole, benzoxazole, benzthiazole, benzimidazole, 3,4-dihydro 4-oxo-2H-benzo[e]oxazine, 1-(methyl or ethyl)benzimidazole, each of these ring systems being linked to (CH2)$_q$ through carbon and each ring system being optionally substituted by fluorine, chlorine, bromine, methyl, ethyl, n-propyl, isopropyl, trifluoromethyl, cyclopropylmethyl, formamido, carboxy, methoxycarbonyl, ethoxycarbonyl, methoxy, ethoxy, cyano, 3-cyanoallyl, carbamoyl, methylcarbamoyl, dimethylcarbamoyl, hydroxy, guanidino, nitro or amino, or 2-guanidinothiazol 4-ylmethyl, 3-hydroxybenzoylmethyl, 2-thenyl, 2-imidazolylmethyl or cinnamyl, optionally substituted by fluorine, chlorine, bromine, methyl, ethyl, n-propyl, isopropyl, hydroxy, methoxy, ethoxy, carboxy, methoxycarbonyl, ethoxycarbonyl or carbamoyl;

A particular acid which affords a pharmaceutically acceptable anion is, for example, hydrochloric, hydrobromic, phosphoric, sulphuric, citric or maleic acid.

A particular base which affords a pharmaceutically acceptable cation is, for example, a base containing an alkali metal, (e.g. sodium or potassium) or an alkaline earth metal (e.g. calcium or magnesium), or a primary, secondary or tertiary organic amine (e.g. triethylamine, morpholine, N-methylpiperidine, N-ethylpiperidine, procaine, dibenzylamine or N,N'-dibenzylethylenediamine), or other amine which has been used to form salts with cephalosporins.

The following are preferred features of the cephalosporin derivative of the invention. When any one of these features is taken, either singly or in combination, with the other general or particular features of the cephalosporin derivative of the invention listed above, there are obtained preferred sub-groups of compounds.

1. X is sulphur.
2. R1 is 2-aminothiazol-4-yl or 5-amino-1,2,4-thiadiazol-3-yl.
3. R50 is chloromethylene.
4. R50 is $=N.OR2$ in which R2 is (1–6C)alkyl, (3–6C)alkenyl optionally substituted by carboxy, (3–6C)alkynyl, (3–8C)cycloalkyl, (3–6C)cycloalkyl(1–3C)alkyl, (1–4C)haloalkyl, (1–5C)cyanoalkyl, (2–6C)hydroxyalkyl, (1–4C)alkoxy (2–4C)alkyl, (2–6C)aminoalkyl or benzyl.
5. R2 is methyl, ethyl, i-propyl, allyl, propargyl, cyclopentyl, cyclopropylmethyl, 2-chloroethyl, 2-fluoroethyl, 2-bromoethyl, cyanomethyl, 2-cyanoethyl, 2-hydroxyethyl, 2-ethoxyethyl or benzyl.
6. R2 is of the formula III.
7. In formula III, m is 0.
8. In formula III, R24 is hydroxy or (1–4C)alkoxy.
9. In formula III, R22 and R23 are both hydrogen or (1–3C)alkyl, or R22 and R23 are joined to form, together with the carbon to which they are attached, a (3–7C) carbocyclic ring. 10. In formula III, R22 and R23 are both hydrogen or methyl, or R22 and R23 are joined to form, together with the carbon to which they are attached, a cyclobutane or cyclopentane ring.

Particular compounds of the invention are described in the Examples.

The cephalosporin derivatives of the formula I may be manufactured by methods known in themselves for the manufacture of chemically analogous compounds. The following processes, (R1, R2, R3, R4, R5, R50 and X having the meanings stated above, unless indicated otherwise) are therefore provided as further features of the invention.

The process of the invention is characterised by (a) reaction of a compound of the formula X with a compound of the formula R5—R40 in which R40 is a displaceable radical [e.g. fluorine, chlorine, bromine, (1–6C)alkoxy, (1–6C)alkylthio, (1–6C)alkanesulphinyl or (1–6C)alkane-sulphonyl]:

(b) reaction of a compound of the formula XI with an acid of the formula XII or an activated derivative thereof;

(c) deprotection, to form carboxy, of the corresponding compound which carries a protecting group in place of the acidic hydrogen atom of the carboxyl group;

(d) deprotection, to form a primary or secondary amino group, of the corresponding compound which carries a protecting group in place of the amino hydrogen:

(e) for those compounds in which X is sulphinyl, oxidation of the corresponding compound in which X is sulphur;

(f) reaction of a compound of the formula XII with a compound of the formula R2—O—NH2;

(g) for those compounds in which R2 is other than hydrogen, reaction of a compound of the formula I in which R2 is hydrogen with a compound of the formula R41—R40 in which R40 is a displaceable radical and R41 is one of the values given above for R2, other than hydrogen;

(h) for those compounds which contain an aminophenyl group, the reduction of the corresponding nitrophenyl compound;

(i) the reaction of a compound of the formula XIV wherein R40 is a displaceable radical, with a compound of the formula R4R5NH.

When the process of the invention manufactures the compound of the formula I in the form of the zwitterion, and a salt is required, the compound of the formula I in the zwitterionic form is reacted with an acid which affords a pharmaceutically-acceptable anion, or with a base which affords a pharmaceutically-acceptable cation.

The starting material of the formula X may be prepared by acylation of the appropriate 7-amino-3-azidomethylcephalosporin derivative with an acid of the formula XII, or an activated derivative thereof, followed by reduction of the 3-azidomethyl group to the 3-aminomethyl group. During this process it may be necessary to protect amino and carboxy groups. There is thus obtained the compound of the formula X in which $R^4$ is hydrogen. When R4 is other than hydrogen, the compound in which $R^4$ is hydrogen is then alkylated or benzylated.

The starting material of the formula XI may be prepared by reaction of the compound of the formula XV with a compound of the formula R5—R40 in which R40 is a displaceable radical. During this reaction it may be necessary to protect the 7-amino, 3'-amino and/or 4-carboxy groups.

The starting material of the formula XI is particularly valuable and is regarded as a further feature of the invention.

The starting materials of the formulae XII, XIII, XIV and XV are prepared by conventional methods known in the chemical literature for analogous compounds.

As noted above the cephalosporin derivatives of the invention have antibacterial properties. Thus they are useful antibacterial agents, many of them having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests, and the preferred compounds of this invention have $MIC_{50}$ values of less than 4 μg./ml. against both *Pseudomonas aeruginosa* and *Staphylococcus aureus*.

Cephalosporin derivatives have generally been found to be relatively non toxic to warm-blooded animals, and this generalisation holds true for the compounds of the present invention. A number of compounds were administered to mice at doses in excess of those required to afford protection against bacterial infections, and no overt toxic symptoms or side effects attributable to the administered compounds were noted.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other beta-lactams or aminoglycosides), inhibitors of beta lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in delta relative to tetramethylsilane (delta =0) as internal standard, (s=singlet, d=doublet, t=triplet, q=quartet, m=multiplet, br=broad J=coupling constant). The n.m.r. are measured at a field strength of 90 or 400 MHz. The n.m.r. solvent was $d_6DMSO+CD_3COOD+TFAd$ unless otherwise indicated. The temperatures are in degrees Centigrade. HOAc means acetic acid, and DMF means dimethylformamide.

EXAMPLES 1 and 2

The following compounds were prepared:

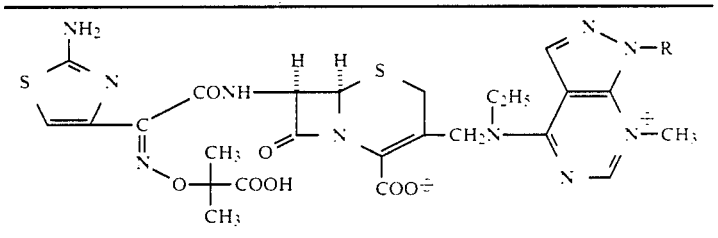

|   | R | Yield (%) | Footnotes |
|---|---|---|---|
| Example 1 | $CH_3$ | 19 | 1,3 |
| Example 2 | H | 38 | 2,3 |

Footnotes
1. To a stirred suspension of 3-ethylaminomethyl-7-[2-(2-aminothiazol-4-yl)-2-((Z)-1-carboxy-1-methylethoxyimino)acetamido]ceph-3-em-4-carboxylic acid (0.2 g, 0.39 mmole) and triethylamine (0.080 ml, 0.58 mmole) in DMF (2 ml) at 25° C. was added the quarternised 1,7-dimethyl-4-methylthiopyrazolo[3,4-d]pyrimidine (0.37 g, 2.8 mmole). The reaction mixture was heated at 50° C. for 3 hours, the solution was evaporated to dryness and the residue purified by preparative HPLC on an octadecylsilane column; nmr 1.35 (m, 3H); 1.6 (s, 6H); 2.6 (s, 3H); 3.5 (d, 2H); 3.9 (s, 2H); 4.2 (s, 3H); 4.9 (d, 1H); 5.3 (d, 1H); 5.4 (d, 1H); 5.9 (d, 1H); 7.04 (s, 1H); 8.66 (s, 1H); 9.01 (s, 1H).
2. The compound was prepared as described in Footnote 1 but using 2.8 mmole of 7-methyl-4-methylthiopyrazolo[3,4-d]pyrimidine; nmr of product 1.3 (m, 3H); 1.5 (s, 6H); 3.4 (m, 2H); 3.9 (s, 5H); 4.9 (d, 1H); 5.2 (m, 2H); 5.8 (d, 1H); 7.0 (s, 1H); 8.7 (s, 1H); 9.0 (s, 1H).
3. The quaternised methylthiopyrazolopyrimidine compounds used in Examples 1 and 2 were prepared by the method of F Bergmann, A Frank and Z Neiman, J Chem. Soc. Perkin I 1979, 2795.

EXAMPLE 3

The following compound:

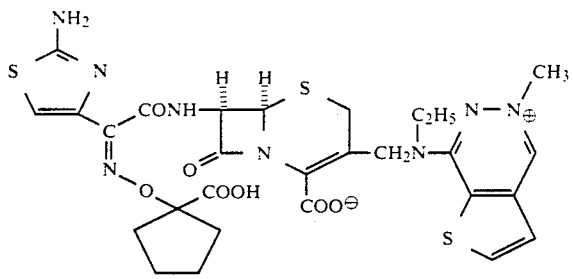

was prepared as follows: 3-Ethylaminomethyl-7-[2-(2-aminothiazol-4-yl)-2-((Z)-1-carboxycyclopentyloxyimono)acetamino]ceph-3-em-4-carboxylic acid (215 mg; 0.4 mmole) was dissolved in DMF (0.5 ml) with stirring and NaHCOhd 3 (96 mg, 1.2 mmole) in solution in water (3 ml) was added. 4-Chloro-6-methylthieno[2,3-d]pyridazinium tetrafluoroborate (130 mg, 0.48 mmole) was added and the mixture heated at 50° C. for 4½ hours with the addition of a further 130 mg of the quaternary heterocycle, and of a further 32 mg (0.4 mmole) of NaHCO$_3$. The mixture was then acidified with HOAc and evaporated. The residue was purified by preparative HPLC on a 'Nucleosil' C-8 column using a gradient of methanol/1%HOAc/H$_2$O 30:70 to 32.5:68.5. The fractions obtained were partially evaporated and lyophilised to yield 80 mg (29%) of the desired product, nmr 1.31 (t, 3 H): 1.7 (m, 4 H): 2.1 (m, 4 H) 3.5 (m, 2 H): 3.95 (q, 2 H): 4.33 (s, 3 H): 4.54(d,1 H,J=16 Hz): 4.95(d,1 H,J=16 Hz): 5.15 (d, 1 H, J=4.8 Hz): 4.85 (d, 1 H, J=4.8 Hz): 7.04 (s, 1 H): 7.94 (d, 1 H, J=5.47 Hz): 8.58 (d, 1 H, J=5.47 Hz): 9.64 (s, 1 H).

The quaternary heterocycle was prepared by dissolving 4 chlorothieno[2,3 d]pyridazine (Bull. Soc. Chem. 4220 (1968)) (256 mg: 1.5 mmole) in dry dichloromethane (10 ml) and adding, with stirring under an inert atmosphere, 222 mg (1.5 mmole) of trimethyloxonium tetrafluoroborate. After 4 hours the solids were removed by filtration yielding 340 mg (85%) of the required compound, nmr in DMSOd$_6$ 4.63 (s, 3 H); 8.30 (d, 1 H, J=5.2 Hz) 8.91 (d, 1 H, J=5.2 Hz): 10.41 (s, 1 H).

EXAMPLES 4 6

The following compounds were prepared:

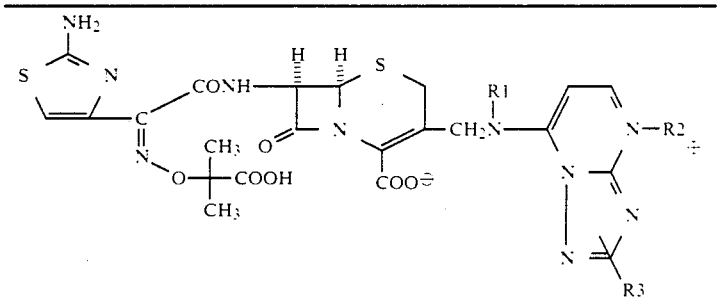

| Example No. | R1 | R2* | R3* | Yield (%) | Footnotes |
|---|---|---|---|---|---|
| 4 | H | CH$_3$ | — | 31 | 1,2 |
| 5 | C$_2$H$_5$ | CH$_3$ | — | 5 | 3,2 |
| 6 | C$_2$H$_5$ | — | CH$_3$ | 20 | 3,2 |

*where (—) is indicated the group concerned is absent.
Footnotes
1. To a stirred solution of 3-aminomethyl-7-[2-(2-aminothiazol-4-yl)-2-((Z)-1-carboxy-1-methylethoxyimino)acetamido]ceph-3-em-4-carboxylic acid (250 mg, 0.5 mmole) and triethylamine (0.1 ml, 0.7 mmole) in DMF (5 ml) at 25° C. was added the quaternised 7-methylthio-1,2,4-triazolo[2,3-a]pyrimidine prepared as in Footnote 2 as a mixture of two isomers (300 mg, 1.1 mmole). After one hour at room temperature the solution was evaporated to dryness and the residue purified by preparative HPLC on an octadecylsilane column, nmr 1.5 (s, 6H); 3.5 (s, 2H); 4.0 (br, 3H); 4.7 (s, 2H); 5.15 (d, 1H); 5.85 (d, 1H); 7.0 (m, 2H); 8.6 (m, 2H).
2. The quaternised triazolo pyrimidine starting material was prepared as follows: to a solution of 7-methylthio-1,2,4-triazolo[1,5-a]pyrimidine (1 g, 6 mmoles) in a mixture of methylene chloride (20 ml) and nitromethane (20 ml) was added trimethyloxonium tetrafluoroborate (0.9 g, 6 mmoles). After stirring for 2 hours, the solution was evaporated to dryness; the mixture of two N-methylated isomers produced (according to nmr) was used without further purification in the preparation of the cephalosporin compounds. Nmr of the mixture, 2.9 (s, 3H); 3 (s, 3H); 4 (s, 3H); 4.3 (s, 3H); 7.8 (d, 1H and 1H); 9-9.1 (m, 1H and 2H); 9.6 (s, 1H).
3. To a stirred solution of 3-ethylaminomethyl-7-[2-(2-aminothiazol-4-yl)-2-((Z)-1-carboxy-1-methylethoxyimino)acetamido]ceph-3-em-4-carboxylic acid (250 mg, 0.48 mmole) and triethylamine (0.07 ml, 0.5 mmole) in DMF (2.5 ml) was added the mixture of the two N-methylated 7-methylthio-1,2,4-triazol[1,5-a]-pyrimidines (Footnote 2) (300 mg, 1.1 mmoles). The mixture was stirred at 40° C. for 2 hours and then evaporated to dryness and purified by preparative HPLC on an octadecylsilane column, yielding two isomeric compounds, nmr:
1.25 (m, 3H); 1.5 (br, 6H); 3.5 (s, 2H); 3.95 (br, 5H); 5.15 (d, 3H); 5.85 (d, 1H); 7.0 (m, 2H); 8.6 (m, 2H) (Example 5) and 1.2 (br, 3H); 1.5 (s, 6H); 3.45 (s, 2H); 3.8 (m, 5H); 5.2 (m, 3H); 5.8 (d, 1H); 7.0 (m, 2H); 8.45 (m, 1H); 9.3 (s, 1H) (Example 6). The position of the methyl group R3 in the compound of Example 6 could not be assigned.

EXAMPLE 7

The following compound:

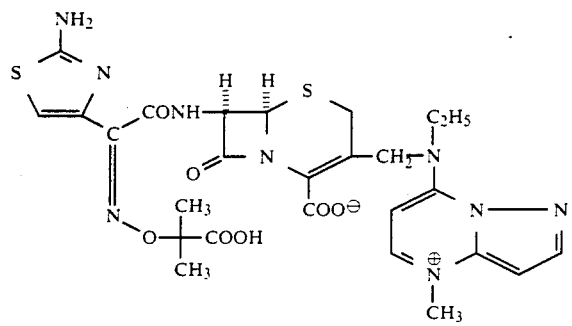

was prepared as follows,

To a stirred solution of 3-ethylaminomethyl-7-[2-(2-aminothiazol 4-yl)-2-((Z)-1-carboxy-1-methylethoxyimino)acetamido]ceph-3-em-4-carboxylic acid (250 mg, 0.48 mmole) and triethylamine (0.07 ml, 0.5 mmole) in DMF (2.5 ml) was added 4-methyl 7-methylthio pyrazolo [1,5-a]pyrimidinium tetrafluroborate (0.3 g, 1.1 mmoles). The mixture was stirred at 40° C. for 1 hour, evaporated to dryness and purified by preparative HPLC on an octadecylsilane column, nmr 1.3 (br, 3 H) 1.5 (s, 6 H): 3.55 (s, 2 H): 3.95 (m, 5 H): 5.1–5.9 (m, 4 H): 6.7 (m, 2 H): 7.0 (s, 1 H): 8.35 (m, 2 H).

The quaternised pyrazolo [1,5-a]pyrimidine starting material was prepared as follows: To a solution of 7-methylthiopyrazolo[1,5-a]pyrimidine (1 g, 6 mmoles) in methylene chloride (25 ml) was added trimethyloxonium tetrafluoroborate (1 g, 6.7 mmoles). After stirring at room temperature for 1 hour, the solid was filtered and used without further purification, nmr 2.93 (s, 3 H): 4.27 (s, 3 H): 7.2 (d, 1 H) 7.55 (d, 1 H): 8.6 (d, 1 H): 9.0 (d, 1 H). Yield 27%.

EXAMPLE 8

The following compound,

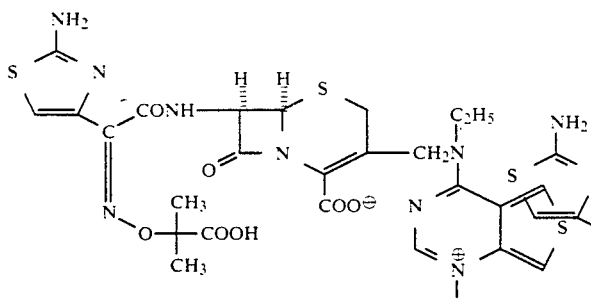

was prepared as follows:

To a stirred solution of 3-ethylaminomethyl-7-[2-(2-aminothiazol-4-yl) 2-((Z)-1-carboxy-1-methylethoxyimino)acetamido]ceph-3-em-4-carboxylic acid (300 mg, 0.58 mmole) and triethylamine (0.080 ml, 0.58 mmole) in DMF (3 ml) was added 1-methyl-4-methylthiothieno[3,4-d]pyrimidinium tetrafluoroborate (166 mg, 0.58 mmole). The mixture was stirred for 1 hour at room temperature, evaporated to dryness and purified by preparative HPLC on an octadecylsilane column, nmr 1.5 (br, 9 H): 3.45 (s, 2 H): 3.9 (s, 3 H): 4 (m, 2 H); 4.7–5.5 (m, 3 H): 5.8 (d, 1 H): 7.0 (s, 1 H): 8.0 (s, 1 H): 8.5 (s, 1 H): 8.9 (s, 1 H). Yield 8%.

The quaternised thieno pyrimidine starting material was prepared as follows: to a solution of 4-methylthiothieno[3,4-d]pyrimidine (1 g, 5.5 mmole) in methylene chloride (80 ml) was added trimethyloxonium tetrafluoroborate (730 mg, 4.8 mmole). After stirring overnight, the solid was filtered and washed with methylene chloride. Nmr (in DMSOd$_6$): 2.92 (s, 3 H): 4.22 (s, 3 H): 8.6 (d, 1 H): 9.25 (m, 2 H).

The compound 3-ethylaminomethyl-7-[2-(2-aminothiazol-4-yl)-2-((Z)-1-carboxy-1-methylethoxy imino)acetamido]ceph 3 em 4-carboxylic acid used as starting material in Examples 1, 2, 5, 6 and 8 may be obtained by reductive amination of acetaldehyde (1.1 eq) with 3-aminomethyl-7-[2-(2-aminothiazol-4-yl)-2-((Z)-1-carboxy 1-methylethoxyimino)-acetamido]ceph-3-em-4-carboxylic acid (1.0 eq) in the presence of NaBH$_3$CN (1.0 eq) and Et$_3$N (1.0 eq). The acetaldehyde is added dropwise at room temperature in methanol, and the mixture stirred for ½ hour. The product may be purified by preparative HPLC e.g. using methanol/-H$_2$O/HOAc 10:90:1 v/v/v, followed by 15:85:1.

The compound 3-ethylaminomethyl-7-[2-(2-aminothiazol-4-yl)-2-((Z)-1-carboxycyclopentyloxyimino)acetamido]ceph-3-em-4-carboxylic acid used as starting material in Example 3 may be prepared by an analogous method starting from 3-aminomethyl-7-[2-(2-aminothiazol4-yl) 2-((Z-1-carboxycyclopentyloxyimino)acetamido]ceph-em-4-carboxylic acid.

EXAMPLE 9

The following compound:

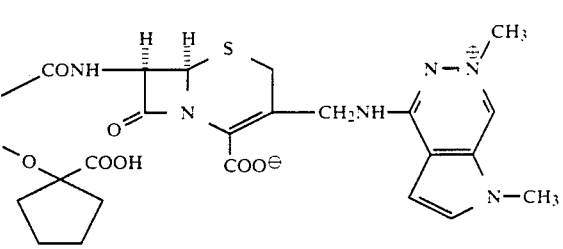

was prepared as follows:
3-aminomethyl-7-[2-(2-aminothiazol-4-yl)-2-((Z)-1-carboxycyclopentyloxyimino)acetamido]ceph-3-em-4-carboxylic acid (204mg: 0.4 mmole) was suspended in DMF (2 ml) with stirring and NaHCO$_3$ (96mg. 1.2 mmole) in solution in water (2 ml) was added. 4-chloro-1,6-dimethyl-4-pyrrolo-[2,3-d]pyridazinium tetrafluoroborate (129 mg. 0.48 mmole) in solution in DMF (2 ml) was added and the mixture heated at 55° C. for 3 hours. The mixture was then acidified with AcOH and evaporated. The residue was purified by preparative HPLC on a 'Nucleosil' C-18 column using methanol/H₂O -1% AcOH 35:65 as eluant. The fractions obtained were partially evaporated and lyophilised to yield 97μg (37%) of the desired product, Nmr, 1.87(m,4 H): 3.15(m,4 H): 3.22–3.86(m,2 H): 3.96(s,3 H): 4.22(s,3 H): 4.1(d,1 H): 4.8 (d,1 H): 5.11(d,1 H): 5.8(d,1 H): 7.04(s,1 H): 7.05(d,1 H): 7.89(d,1 H): 9.51(s,1 H).

The quaternary heterocycle was prepared by dissolving 4-chloro-1-methyl-4-pyrrolo[2,3-d]pyridazine (Chimie Therapeutique 3, 348 (1968)) (352mg 2.1 mmole) : in dry dichloromethane (2 ml) and adding 129mg (0.48mmole) of trimethyloxonium tetrafluoroborate. After stirring for 4 hours, the solids were removed by filtration yielding 500 mg (88%) of the required compound. Nmr in DMSOd₆, 4.17 (s, 3 H); 4.53 (s,3 H); 7.27(d, 1 H); 8.54(d, 1 H); 10.39(s, 1 H).

EXAMPLE 10

The following compound was prepared as follows:

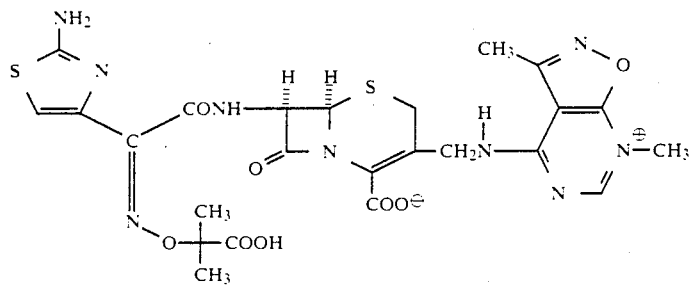

To a stirred solution of 3-aminomethyl-7-[2-(2-aminothiazol-4-yl)-2-((Z)-1-carboxy-1-methylethoxyimino)acetamido)ceph-3-em-4-carboxylic acid (500mg, 1 mmole) and triethylamine (0.145 ml, 1 mmole) in DMF (4 ml) was added the quaternised 3,7 dimethyl-4-methylthioisoxazolo[5,4-d]pyrimidinium tetrafluoroborate (292mg, 1 mmole). The mixture was stirred at 40° C. for 45min, evaporated to dryness and purified by preparative HPLC on an octadecylsilane column: yield: 10%. Nmr: 1.5 (s,6 H): 2.7(s,3 H): 3.2–3.8(m,2 H): 4(s,3 H): 4.6 and 5(AB,2 H): 5.1(d,1 H): 5.9(d,1 H): 7(s,1 H): 8.9(s,1 H).

The quaternised isoxazolo-pyrimidinium starting material was prepared as follows:

To a solution of 3-methyl-4-methylthio isoxazolo[5,4-d]pyrimidine (3 g, 0.016 mole) in methylene chloride (50 ml) was added trimethyloxonium tetrafluoroborate (2.3 g, 0.016 mole). The mixture was stirred at 20° C. overnight. After evaporation, the solid was saturated with ether and used without further purification:

Nmr (DMSOd₆+CD₃COOD+TFAd): 2.7(s,3 H); 2.9(s,3 H); 4.2(s,3 H); 9.4(s,1 H). Yield: 70%.

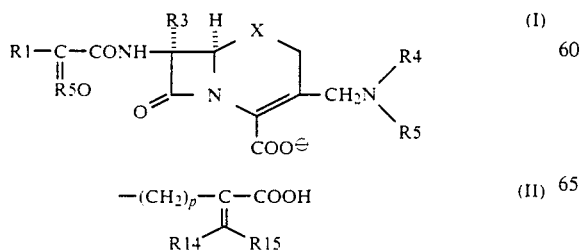

(I)

$-(CH_2)_p-C-COOH$ (II)

-continued

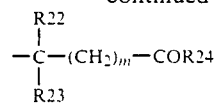

(III)

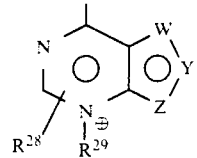

(IV)

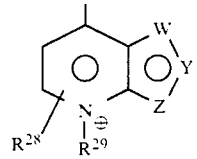

(V)

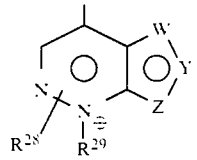

(VI)

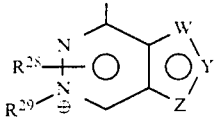

(VII)

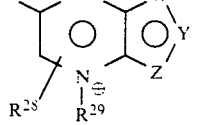

(VIII)

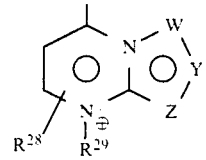

(IX)

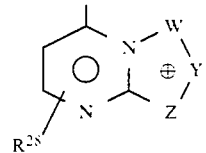

(X)

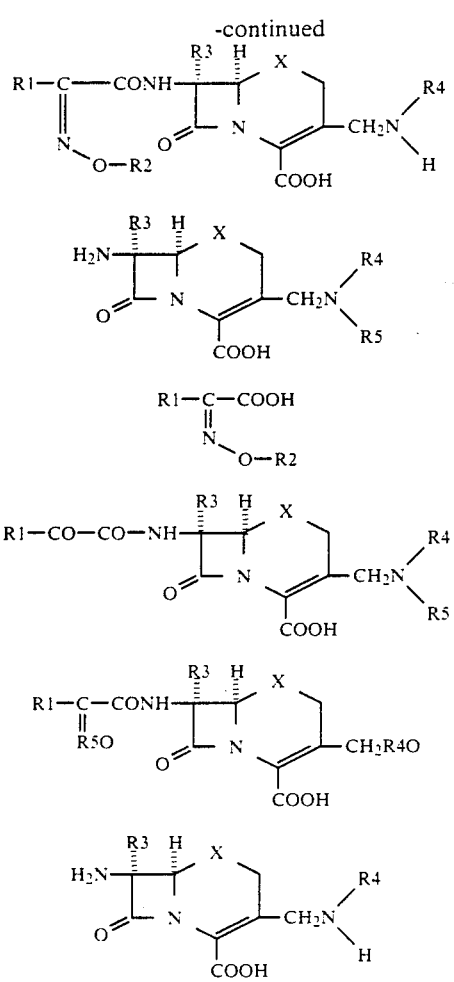

We claim:

1. A cephalosporin derivative of the formula I in which X is sulphur or sulphinyl (R or S configuration):

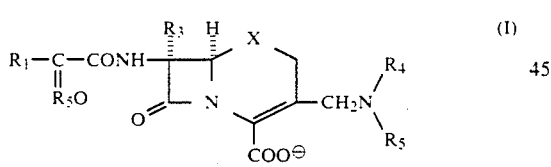

R1 is 2-aminooaxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R50 is chloromethylene or a radical of the formula =N.O.R2, wherein R2 is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C) cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4-C)alkyl, (1-4C)haloalkylxcarbamoyl(1-4C)alkyl, triphenylmethyl, (1-3C)haloalkyl, (2-6C)hydroxyalkyl, (1-4C)alkoxy(2-4C)alkyl, (1-4C)alkylthio(-2-4C)alkyl, (1-4C)alkanesulphinyl(1-4C)alkyl, (1-4C)alkanesulphonyl(1-4C)alkyl, (2-6C-)aminoalkyl, (1-4C)alkylamino(1-6C)alkyl, (2-8C-)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3yl, 2-oxopyrrolidinyl, or 2-oxotetrahydrofuran-3-yl, or —R2 is of the formula —(CH$_2$)$_n$—R6 in which n is 1 to 4 and R6 is piperidino, pyrrolidino, morpholino, piperazino or N-methylpiperazino, each value of R6 being optionally substituted by (1-4C)alkyl, phenyl or benzyl, or —R2 is of the formula —(CH$_2$)$_m$—W—R7 in which m is 0 to 3, W is sulphur or a direct bond, and R7 is phenyl or pyridinio(1-4C)alkylene or R7 is pyridinyl, imidazolyl, 1,3,4-thiadiazolyl, tetrazolyl, 1-(1-4C)alkyltetrazolyl, thiazolyl, isothiazolyl or isoxazolyl in which the link with W is via a carbon or uncharged nitrogen, each value of R7 being optionally substituted, where possible, by one or two groups selected from (1-4C)alkyl, amino, hydroxy, carboxy, carbamoyl, nitro, (2-5C-)alkoxycarbonyl, cyano or sulpho, or —R2 is of the formula —(CH$_2$)$_n$—CO—R8 in which n is 1 to 4 and R8 is (1-4C)alkyl, phenyl or benzyl, or 13R2 is of the formula —COR9 or —(CH$_2$-)$_n$—OCO—R9 in which n is 1-4 and R9 is hydrogen, (1-4C)alkyl, (1-4C)haloalkyl, phenyl or benzyl, such as phenyl or benzyl group being optionally substituted by 1,2, or 3 substituents selected from (1-6C)alkyl, (2-6C)alkanoyloxy and hydroxy groups.

or —R2 is of the formula —G—CH$_2$—R10 in which G is carbonyl or a direct bond and R10 is phthalimido, or —R2 is of the formula II

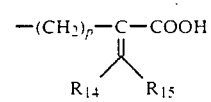

in which p is 1 or 2 and R14 and R15 are hydrogen or (1-4C)alkyl, or —R2 is of the formula —P(O)R16R17 in which R16 is hydroxy, (1-4C)alkoxy, (2-8C)dialkylamino, phenoxy, phenylamino or one of the values given above for R6, and R17 is (1-C)alkyl, (1-4C)alkoxy (2-8C)dialkylamino, phenoxy, phenylamino, piperidino, pyrrolidino, morpholino, piperazino or N-methylpiperazino, or —R2 is of the formula —CH$_2$P(O)R18R19 in which R18 and r19 are hydroxy or (1-4C)alkoxy, or —R2 is of the formula —CH(SR20)COOR21 in which R20 is (1-4C)alkyl and R21 is hydrogen or (1-6C)alkyl, or —R2 is of the formula III

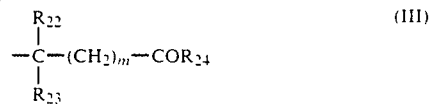

in which n is 0-3, R22 is hydrogen, (1-3C) alkyl or methylthio, R23 is hydrogen, (1-3C)alkyl, (C$_3$-C$_7$)-cycloalkyl, cyano, carboxy, (2-5C)carboxyalkyl or methanesulphonylamino, or phenyl optionally substituted by amino or hydroxy, or R22 and R23 are joined to form, together with the carbon to which they are attached, a (3-7C) carboxylic ring, and R24 is hydroxy, amino, (1-4C)alkoxy, (1-4C)alkylamino, phenylamino or of the formula R6 given above or of the formula NHOR25 in which R25 is hydrogen, (1-C)alkyl, phenyl or benzyl, or R2 is of the formula —$\xi$CH(COOH)Ph wherein Ph represents a benzene ring optionally substituted by 1, 2 or 3 substituents selected from (1-6C)alkyl, (2-6C)alkanoyloxy and hydroxy groups and wherein the chiral centre denoted by $\xi$ may have either the R or S absolute configuration or be a racemate thereof; provided that when R2 contains phenyl, and unless otherwise stated, the phenyl is optionally substituted by 1 or 2 groups selected from halogen, hydroxy, amino, carboxy, nitro, carbamoyl, cyano and aminomethyl, R3 is hydrogen or methoxy;

R4 is hydrogen, (1-4C)alkyl, halo(1-4C)alkyl, hydroxy(1-4C)alkyl, (1-4C)alkoxy(1-4C)alkyl, carboxy (1-4)alkyl, amino (1-4C)alkyl, cyano(1-4C)alkyl, (1-4C)alkanoylamino(1-4C)alkyl, allyl, furfuryl, benzyl or pyridyl(1-4C)alkyl;

R5 is an aromatic heterocyclic fused ring system which is linked via carbon and is one of the formula IV to X

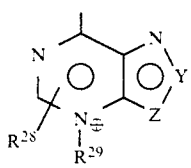 (IV)

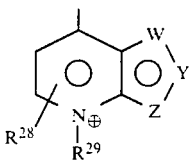 (V)

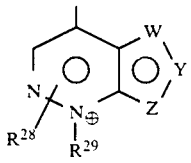 (VI)

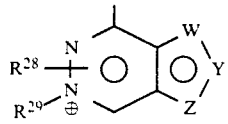 (VII)

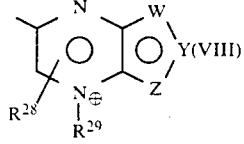 (VIII)

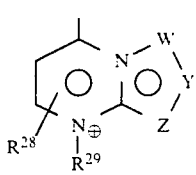 (IX)

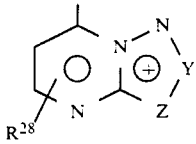 (X)

inclusive in which W, Y and Z are selected from O, S, N, CR$^{26}$ (in which R$^{26}$ is selected from hydrogen, halogen, (1-5C)alkyl, carboxy, (2-6C)alkoxycarbonyl, (2-6C)-alkoxycarbonyl(1-4C)cyanoalkyl, amino, (1-6C)alkylamino, (2-8C)dialkylamino, benzylamino (optionally substituted in the benzene ring thereof by nitro), thenylamino, allylamino, (1-6C)aminoylamino, (1-6C)alkoxy(1-6C)alkylamino, (1-6C)hydrpxyalkylamino, hydroxy, mercapto, carbamoyl, (2-6C)alkylcarbamoyl, (3-10C)dialkylcarbamoyl, phenylthio and heteroarylthio wherein heteroaryl is a 5- or 6-membered ring containing 1, 2 or 3 hetero atoms selected from oxygen, nitrogen and sulphur) and NR$^{27}$ (in which R$^{27}$ is selected from hydrogen, (1-6C)alkyl, phenyl or benzyl, which alkyl, phenyl or benzyl groups may be substituted when and where possible by one or two groups selected from halogen, nitrogen, (1-6C)alkyl, hydroxy, (1-4C)alkoxy, carboxy, cyano, (2-6C)alkoxycarbonyl, carbamoyl, sulphamoyl, sulpho, mono-or di(1-4C)alkylcarbamoyl, or mono- or di-(1-4C)alkylsulphamoyl) provided that:

(i) only one of W, Y and Z can represent S or O;

(ii) in formulae IV and V, Y must be other than CR$^{26}$;

(iii) formula V one of W and Z must be other than CR$^{26}$; and (iv) in formula IX neither W nor Z can be S and W cannot be O;

R$^{28}$ is attached to carbon and is selected from the atoms and groups listed above in respect of R$^{26}$; and R$^{29}$ is selected from hydrogen, (1-6C)alkyl, (1-6C)alkyl(2-6)alkenyl, (1-6C)alkoxy, (2-8C)alkoxyalkyl, carboxy(1-6C)alkyl, carbonyl(1-6C)alkyl, [(1-6C)alkoxy]carbamoyl(1-6C)alkyl, mono- or di(1-4)alkylamino(1-6C )alkyl, [(1-6C)]carbonylaminocarbonyl(1-6C)alkyl, methyl, benzoylmethyl(1-6C)hydroxyalkyl, amino, (1-6C)alkylamino, (1-6C)aminoalkyl, phenyl(1-6C)alkyl, phenyl(1-6C)alkoxy, (3-6C)cycloalkyl, (3-6C)cycloalkenyl, cyano(3-6C)cycloalkenyl, mono- or di-(1-4)alkylcarbamoyl(1-6C)alkyl or (1-4C)alkoxy(2-4C)alkoxy(-1-4C)alkyl; or phenyl optionally substituted by 1 or 2 groups selected from halogen, (1-6C)alkyl, (1-6C)alkoxy, hydroxy, amino, carboxy, nitro, carbamoyl, cyano, trifluoromethyl, aminomethyl, (1-4C)alkanoyl, (1-4C)alkanoylamino, halo(1-4C)alkyl, (2-6)alkoxycarbonyl, mono- or di(1-4C)alkylcarbamoyl, mesyl, vinyl, sulpho, sulphamoyl, or mono- or di(1-4C)alkylsulphamoyl; or (2-6C-

)alkenyl optionally substituted by halogen, cyano, carbamoyl, mono-or di-(1–4C)alkylcarbamoyl, piperidinocarbonyl, morpholinocarbonyl, 2-ureidoethyl, 2-thioureidoethyl, 2-(thioacetylamino)ethyl, sulphamoyl, 2-amino-2-carboxyethyl, acetylaminomethyl, phthalimidomethyl, 4-5-dihydroimidazol-2-ylmethyl, 3,4,5,6-tetrahydropyrimidin-2-ylmethyl, 2-(1,2,3,6-tetrahydro-2,6-dioxopurin-7-ylethyl, 2-hydroxyiminopropyl (syn or anti) or 2propyl (syn or anti) or cyano(1–4C)alkyl;

or $R^{29}$ is of the formula —(CH$_2$)$_2$- NR30R31R32 in which R30, R31 and R32 are (1–4C)alkyl, or $R^{29}$ is of the formula —(CH$_2$)$_q$—R33 in which q is 0—2 and —R33 is pyridine, pyridazine, pyrimidine, pyrazine, 1,2,5,6-dihydro-5,6-dioxo-1,2,4-triazine, 2-[(1–C)alkyl]-1,2,5,6-dihydro-5,6-dioxo-1,2,4-triazine, 1-[(1–4C)alkyl tetrazole, furan, thiophene, pyrrole, 1-[(1–4C)alkyl]pyrrole, oxazole, thiazole, imidazole, 1-[(1–4C)alkyl]imidazole, isoxazole, isothiazole, pyrazole, 1,2,3-thiadiazole, 1-[(1–6C)alkyl]pyrazole, benzfuran, benzthiophene, indole, oxindole, 1-[(1–6C)alkyl]indole, benzoxazole, benzthiazole, benzimidazole, 1-[(1–6C)alkyl]benzimidazole, 3,4-dihydro-4-oxo-2H-benzo[e]oxazine each of these ring systems being linked to (CH$_2$)$_q$ through carbon and each ring system being optionally substituted by halogen, amino, (1–6C)alkyl, (1–6C)haloalkyl, (3–6C)cycloalkyl, (2–6C)alkenyl, carboxy, (2–6C)alkoxycarbonyl, (-6C)alkoxy, cyano, (2–6C)cyanoalkenyl, carbamoyl, mono- or di(1–4C)alkylcarbamoyl, (1–6C)alkanoylamino, guanidino, hydroxy, nitro or amino;

or R29 is 2-guanidino-thiazol-4-ylmethyl, hydroxybenzoyl-methyl, 2-thenyl, 2-imidazolylmethyl or cinnamyl, optionally substituted by halogen, (1–6)alkyl, hydroxy, (1–6C)alkoxy, carboxy, (2–6C)alkoxycarbonyl, nitro or carbamoyl;

or R29 is —(CH$_2$)$_t$NHCOR34 or —(CH$_2$)$_t$S(O)$_s$—R34 in which t is 1-6, s is 0, 1 or 2, and R34 is (1–6C)alkyl or (1–6C)alkoxy, or R29 is of the formula (CH$_2$)$_2$N=CR36NR37R38 or —(CH$_2$)$_n$ C(NR36)NR37R38 or a tautomer thereof in which n is 1-6 and R36, R37, R38 are hydrogen or (1–4C)alkyl;

and the N-oxides thereof where chemically possible; and the pharmaceutically acceptable acid-addition and base-addition salts thereof.

2. The compound as claimed in claim 1 wherein $R^5$ is of formula (IV) or (V).

3. The compound according to claim 1 wherein $R^5$ is of the formula (VI) or (VII).

4. The compound according to claim 1 wherein $R^5$ is of the formula (VIII).

5. The compound according to claim 1 wherein $R^5$ is of the formula (IX) or (X).

6. A compound as claimed in claim 1 wherein R50 is =N.OR2 wherein R2 is of the formula III wherein m is O, R24 is hydroxy or (–4C)alkoxy, R22 and R23 are both hydrogen or (1–3C)alkyl or R22 and R23 are joined to form, together with the carbon to which they are attached, a (3–7C)carboxylic ring.

7. A compound as claimed in claim 1 wherein R50 is =N.OR2 wherein R2 is (1–6C)alkyl, (3–6)alkenyl optionally substituted by carboxy, (3–6C)alkynyl, (3–8C)cycloalkyl, (3–6C)cycloalkyl(1–3C)alkyl, (1–4C)haloalkyl, (1–5C)cyanoalkyl, (2–6C)hydroxyalkyl, (1–4C)alkoxy-(2–4C)alkyl, (2–6C)aminoalkyl or benzyl.

8. A compound as claimed in claim 1 wherein X is sulphur.

9. A compound as claimed in claim 9 wherein R1 is 2-aminothiazol-4-yl or 5-amino-1,2,4-thiadiazol-3-yl.

10. A pharmaceutical composition comprising an antibacterially effective amount of the compound as claimed in claim 1 and a pharmaceutically acceptable diluent or carrier.

11. A method of treating a warm-blooded animal having a bacterial infection comprising administering to said animal an amount of said compound according to claim 1, sufficient to effect said treatment.

12. A compound of formula:

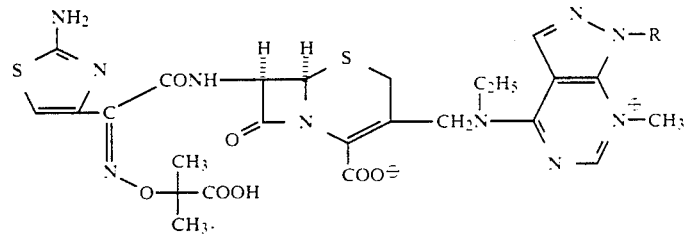

50 wherein R is H or CH$_3$, or pharmaceutically acceptable salt thereof.

13. A compound of formula:

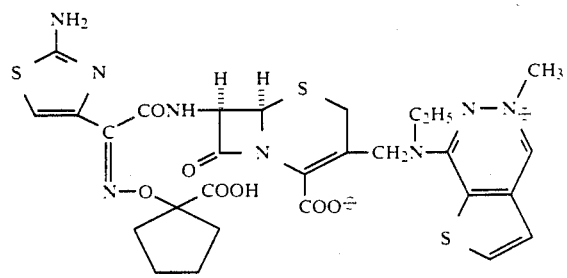

or pharmaceutically acceptable salt thereof.

14. A compound of formula:

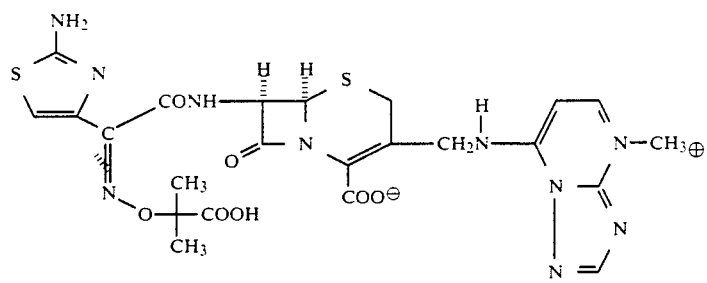
or pharmaceutically acceptable salt thereof.
15. A compound of formula:
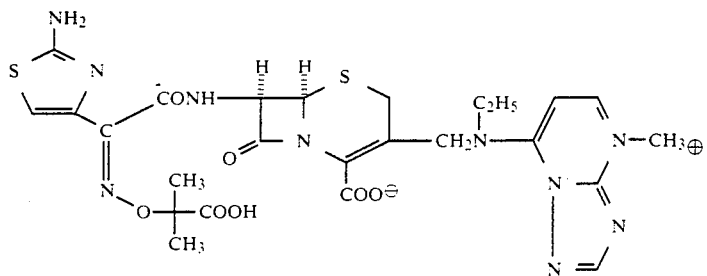
or pharmaceutically acceptable salt thereof.
16. A compound of formula:
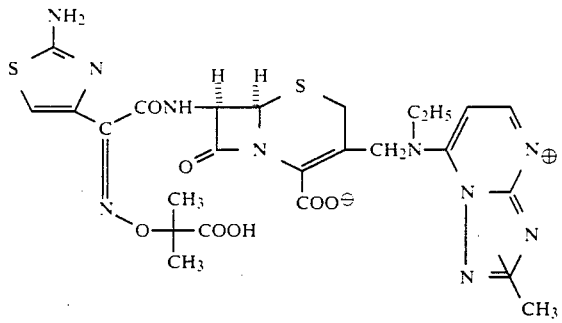
or pharmaceutically acceptable salt thereof.
17. A compound of formula:
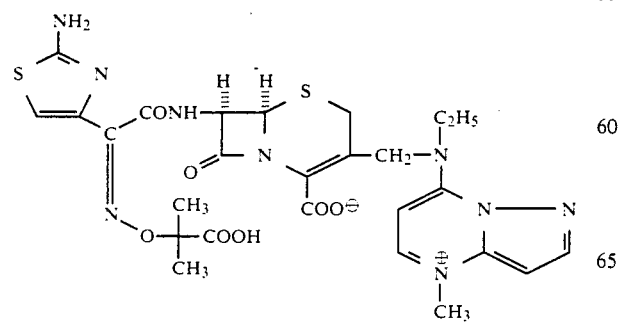
or pharmaceutically acceptable salt thereof.
18. A compound of formula:
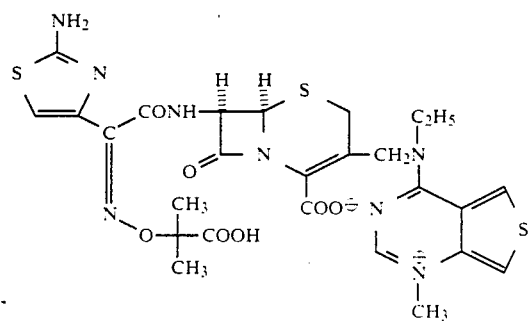
or pharmaceutically acceptable salt thereof.
19. A compound of formula:

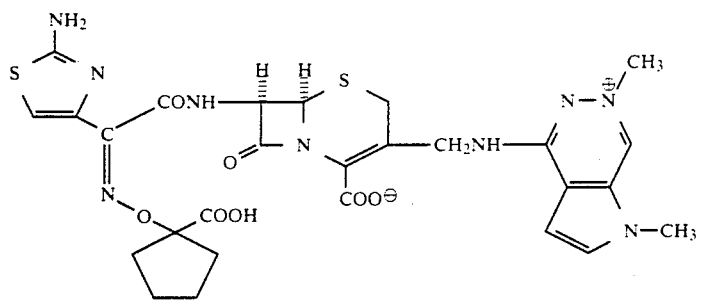
or pharmaceutically acceptable salt thereof.
20. A compound of formula:
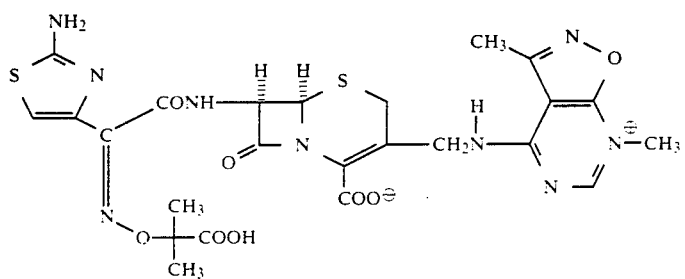
or pharmaceutically acceptable salt thereof.